(12) United States Patent
Loewy et al.

(10) Patent No.: US 8,747,914 B2
(45) Date of Patent: *Jun. 10, 2014

(54) ANTI-INFLAMMATORY DISSOLVABLE FILM

(75) Inventors: Zvi G. Loewy, Fair Lawn, NJ (US);
William Zev Levine, Jerusalem (IL);
Aron J. Saffer, Bet Shemesh (IL)

(73) Assignee: Izun Pharmaceuticals, Inc., New York, NY (US)

( * ) Notice: Subject to any disclaimer, the term of this patent is extended or adjusted under 35 U.S.C. 154(b) by 323 days.

This patent is subject to a terminal disclaimer.

(21) Appl. No.: 13/236,094

(22) Filed: Sep. 19, 2011

(65) Prior Publication Data
US 2012/0003292 A1  Jan. 5, 2012

Related U.S. Application Data

(63) Continuation of application No. 11/765,587, filed on Jun. 20, 2007, now Pat. No. 8,021,696.

(60) Provisional application No. 60/805,240, filed on Jun. 20, 2006.

(51) Int. Cl.
*A01N 65/00* (2009.01)

(52) U.S. Cl.
USPC ........................................ 424/725

(58) Field of Classification Search
None
See application file for complete search history.

(56) References Cited

U.S. PATENT DOCUMENTS

| | | | |
|---|---|---|---|
| 5,788,982 A | 8/1998 | Nadoolman et al. |
| 5,900,247 A | 5/1999 | Rault et al. |
| 6,348,503 B1 | 2/2002 | Squires |
| 6,355,229 B1 | 3/2002 | Adamy |
| 6,576,267 B2 | 6/2003 | Gelber et al. |
| 6,721,987 B2 | 4/2004 | McDevitt et al. |
| 6,756,051 B1 | 6/2004 | Chen et al. |
| 7,008,628 B2 | 3/2006 | Ron et al. |
| 7,033,606 B1 | 4/2006 | Besse et al. |
| 7,285,295 B2 | 10/2007 | Levine |
| 2003/0003140 A1 | 1/2003 | Domb et al. |
| 2003/0193790 A1 | 10/2003 | Nakayabu |
| 2004/0057908 A1 | 3/2004 | Bowen et al. |
| 2004/0151789 A1 | 8/2004 | Levine et al. |
| 2005/0100612 A1 | 5/2005 | Capps |
| 2005/0118217 A1 | 6/2005 | Barnhart et al. |
| 2006/0002987 A1 | 1/2006 | Bevacqua et al. |
| 2007/0053849 A1 | 3/2007 | Doyle et al. |
| 2007/0292487 A1 | 12/2007 | Loewy et al. |

FOREIGN PATENT DOCUMENTS

| | | |
|---|---|---|
| DE | 102005003387 A1 | 3/2006 |
| JP | 7010722 A1 | 6/1993 |
| WO | 02085119 A1 | 10/2002 |
| WO | 02094300 A1 | 11/2002 |

OTHER PUBLICATIONS

Supplementary European Search Report for PCT Application Number PCT/US2007071638 mailed Mar. 3, 2011.
International Search Report and Written Opinion of Internation Searching Authority for PCT Application No. PCT/US07/71638 mailed Nov. 14, 2007.

*Primary Examiner* — Michael Meller
(74) *Attorney, Agent, or Firm* — Moser Taboada

(57) ABSTRACT

Provided, among other things, is a slowly dissolvable film comprising: herbal bioactive agent(s); and polymer(s), dissolvable in the aggregate, wherein the film becomes adhesive as it is placed against a mucosal surface and begins to absorb moisture therefrom.

19 Claims, 2 Drawing Sheets

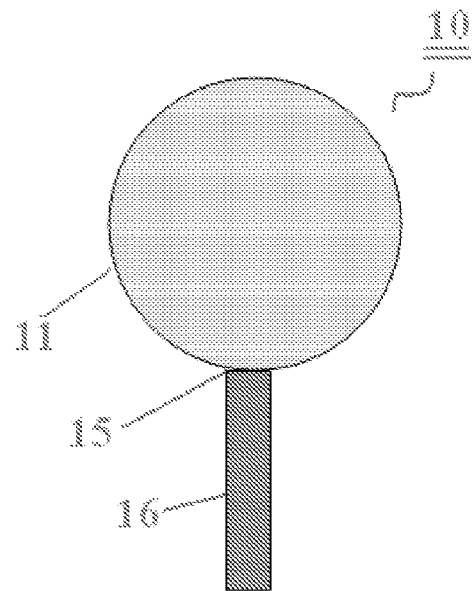
*Fig. 1*
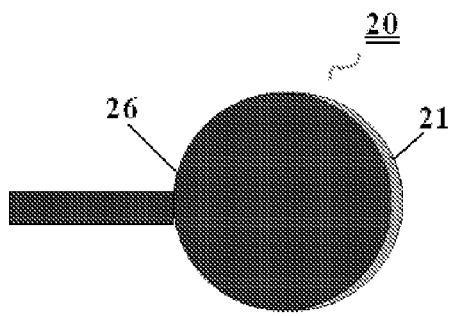 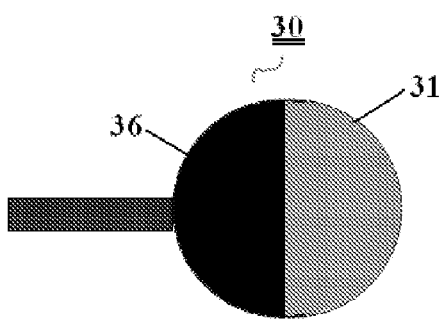
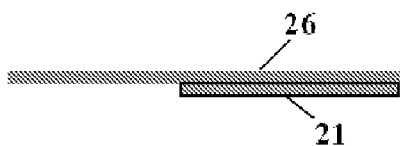 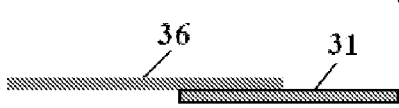
*Fig. 2A*  *Fig. 3A*
*Fig. 2B*  *Fig. 3B*

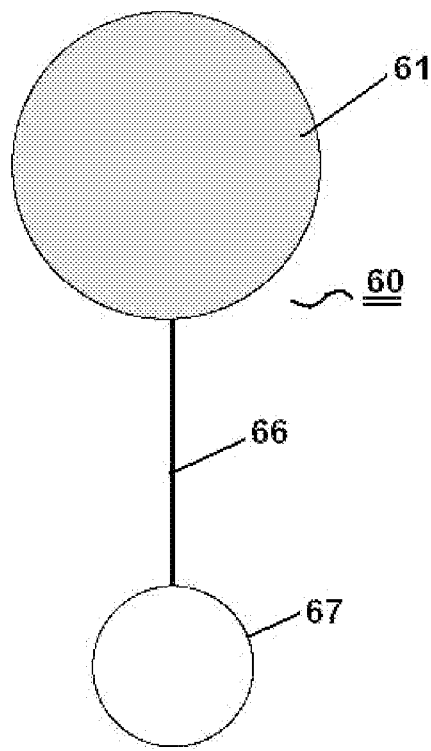
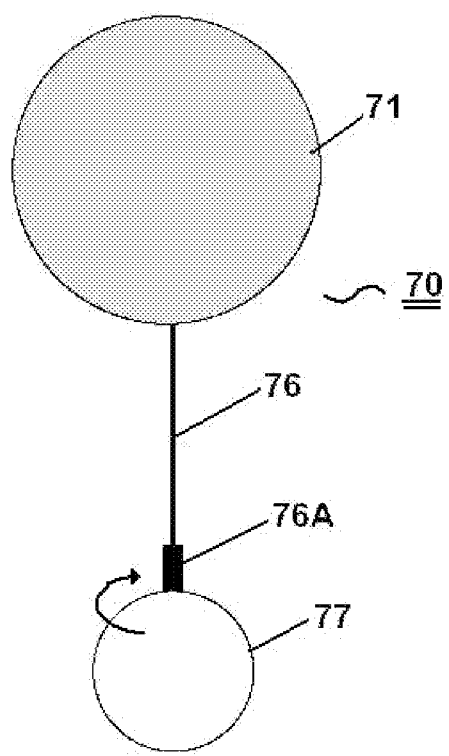
Fig. 4A                Fig. 4B
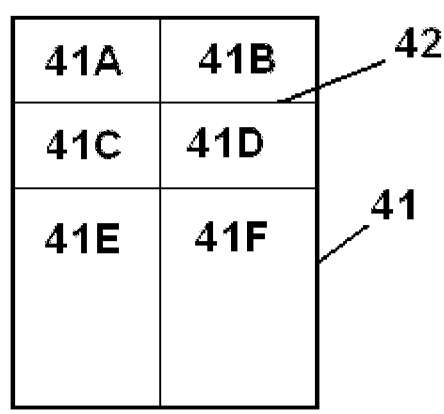
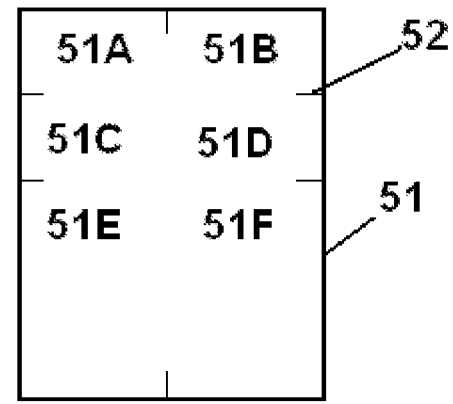
Fig. 5A                Fig. 5B

ANTI-INFLAMMATORY DISSOLVABLE FILM

CROSS-REFERENCE TO RELATED APPLICATIONS

This application is a continuation of U.S. patent application Ser. No. 11/765,587, filed Jun. 20, 2007, now U.S. Pat. No. 8,021,696, issued Sep. 20, 2011, which claims the priority of U.S. patent application Ser. No. 60/805,240, filed Jun. 20, 2006. The aforementioned related patent applications are herein incorporated by reference in its entirety.

The present invention relates to dissolvable films that deliver herbal extracts to mucosal tissue.

Certain herbal extracts have been clinically shown to be effective in treating or ameliorating certain conditions of the mouth. Described in WO 02/094300 and PCT/US05/42348 [corresponding to U.S. Ser. No. 11/284,078, filed 21 Nov. 2005] are a number of useful combinations of herbal extracts for treating or ameliorating diseases of mucosa, and dosage forms for delivering the extracts to discrete regions of the mouth. For example, such combinations, in the delivery form described in PCT/US05/42348, have achieved, in an 80 patient trial, an average of 50% pain reduction in the first ½ hour. In the same trial, average lesion reductions of 40% were achieved in 4 hours.

The delivery devices described in the above-cited documents can be very effective, particularly with discrete lesions. However, in some cases of oral or other mucosal disease the number of lesions can make it at best awkward to apply medicament delivery devices to each of the lesions. Or, the lesions can be located in positions that may make it physically difficult or impossible to deliver a medicament delivery devices to the lesions. Films that adhere upon wetting by mucosal tissue can be used to smoothly adhere to hard-to-reach locations, and can be more adaptable to convoluted tissue surfaces. Also, the typical softness of the film allows films to more comfortably overlap to help cover a mucosal topology. These films are designed to dissolve relatively slowly, with dissolution believed to accentuate release of active in the vicinity of the mucosa, for enhanced uptake. The slow dissolving film in turn protects the lesion from mechanical stress.

SUMMARY OF THE INVENTION

In one embodiment, the invention provides, among other things, a slowly dissolvable film comprising: herbal bioactive agent(s); and polymer(s), dissolvable in the aggregate, wherein the film becomes adhesive as it is placed against a mucosal surface and begins to absorb moisture therefrom.

Further provided is a film application kit comprising: a cosmetic or bioactive agent and a film comprising polymer(s), dissolvable in the aggregate, wherein the film becomes adhesive as it is placed against a mucosal surface and begins to absorb moisture therefrom; and an applicator to which the film is releasable attached such that the film can be placed with the applicator against a mucosal surface to provide sufficient adhesion such that the applicator can be pulled, torn or peeled from the film substantially without displacing the film.

Also provided is a method of treating an indication of mucosal or adjacent tissue comprising periodically applying to mucosa at or adjacent to disease affected tissue a film comprising: herbal bioactive agent(s); and polymers, dissolvable in the aggregate, wherein the film becomes adhesive as it is placed against a mucosal surface and begins to absorb moisture therefrom.

Further provided is a method of applying a film to a mucosal surface comprising: providing:
 a cosmetic or bioactive agent and a film comprising polymer(s), dissolvable in the aggregate, wherein the film becomes adhesive as it is placed against a mucosal surface and begins to absorb moisture therefrom; and
 an applicator to which the film is releasable attached such that the film can be placed with the applicator against a mucosal surface to provide sufficient adhesion such that the applicator can be pulled, torn or peeled from the film substantially without displacing the film from the mucosa; and
manipulating the applicator to position the film on the mucosal surface.

BRIEF DESCRIPTION OF THE DRAWINGS

FIGS. 1-4 show applicator kits useful with the invention.
FIGS. 5A and 5B show films that can be readily divided into subsections.

DETAILED DESCRIPTION OF THE INVENTION

1. Plant Extracts

Appropriate plant extract compositions for use in the film include extract of *Sambucus nigra* (SN), and may include additional plant extracts of *Allium sativum* (AS), *Calendula officinalis* (CO), *Camellia sinensis* (CS), *Centella asiatica* (CA, also known as Gotu Kola), *Commiphora molmol* (CM), *Echinacea purpurea* (EP), *Gaultheria procumbens* (GP), *Hypericum perforatum* (HP), *Krameria triandra* (KT), *Ligusticum porterii-osha* (LP), *Matricaria recutita, Melissa officinalis, Salix alba, Thymus vulgaris, Uncaria tomentosa, Usnea barbata* or *Vaccinium myrtillus*. The extract compositions can include, for example, *Sambucus nigra* extract in an amount from one of the lower percentages (by weight) recited in the next sentence to 90, 95, 96, 97, 98, 99 or 100%. These lower percentages are 50, 55, 60, 65, 70, 75, 80, 85, 90 or 95%. If a second or third extract is present, it may be present, for example in amount from one of the lower percentages to one of the higher percentages recited in the following sentences. Lower percentages for the second or third extracts can be, for example, 0.5, 1, 2, 5, 10 or 20%. Higher percentages can be, for example, 1, 2, 5, 10, 20, 30, 40 or 50%. These ranges, and any other ranges described in this application, can include or exclude one or both endpoints.

The term "extract" is used herein to include all of the many types of preparations containing an effective amount of active ingredients. Thus, the extracts can be produced by cold extraction techniques using a variety of different extraction solvents including, but not limited to, water, fatty solvents (such as olive oil), and alcoholic solvents (e.g. 70% ethanol). Cold extraction techniques are typically applied to softer parts of the plant such as leaves and flowers, or in cases wherein the desired active components of the plant are heat labile. Alternatively, hot extraction techniques can be used, where such solvents are heated to a temperature above room temperature, with the precise value of said temperature being dependent on factors such as the properties of the chosen solvent and extraction efficacy. Hot extraction techniques are more commonly applied to the harder, tougher parts of the plant, such as bark, woody branches and larger roots. In some cases, sequential extractions need to be performed in more than one solvent, and at different temperatures. Standard procedures for producing plant extracts (including hot extraction, cold extraction and other techniques) are described in many publications including "Medicinal plants: a field guide to the medicinal plants of the Land of Israel (in Hebrew), author: N. Krispil, Har Gilo, Israel, 1986 and "Making plant medicine", author: R. Cech, pub. by Horizon Herbs, 2000.

Exemplary extract compositions by weight percentage include:

| Plant Extract | Composition: | | | | | | | | | | | |
|---|---|---|---|---|---|---|---|---|---|---|---|---|
| | C1 | C2 | C3 | C4 | C5 | C6 | C7 | C8 | C9 | C10 | C11 | C12 |
| SN | 70 | 80 | 90 | 70 | 80 | 90 | | | | | | |
| AS | 30 | 20 | 10 | | | | | | | | | |
| CO | | | | 30 | 20 | 10 | | | | | | |
| CA | | | | | | | 30 | 20 | 10 | | | |
| CM | | | | | | | | | | 30 | 20 | 10 |

| | C13 | C14 | C15 | C16 | C17 | C18 | C19 | C20 | C21 | C22 | C23 | C24 |
|---|---|---|---|---|---|---|---|---|---|---|---|---|
| SN | 70 | 70 | 70 | 70 | 70 | 70 | 70 | 70 | 70 | 70 | 70 | 70 |
| AS | 20 | 20 | 20 | 20 | 20 | | | | | | | |
| CO | 10 | | | | | 20 | 20 | 20 | 20 | | | |
| CA | | 10 | | | | 10 | | | | 20 | 20 | 20 |
| CM | | | 10 | | | | 10 | | | 10 | | |
| EP | | | | 10 | | | | 10 | | | 10 | |
| GP | | | | | 10 | | | | 10 | | | 10 |

| | C25 | C26 | C27 | C28 | C29 | C30 | C31 | C32 | C33 | C34 | C35 | C36 |
|---|---|---|---|---|---|---|---|---|---|---|---|---|
| SN | 80 | 80 | 80 | 80 | 80 | 80 | 80 | 80 | 80 | 80 | 80 | 80 |
| AS | 10 | 10 | 10 | 10 | 10 | | | | | | | |
| CO | 10 | | | | | 10 | 10 | 10 | 10 | | | |
| CA | | 10 | | | | 10 | | | | 10 | 10 | 10 |
| CM | | | 10 | | | | 10 | | | 10 | | |
| EP | | | | 10 | | | | 10 | | | 10 | |
| GP | | | | | 10 | | | | 10 | | | 10 |

| | C37 | C38 | C39 | C40 | C41 | C42 | | C44 | C45 | C46 | C47 | C48 |
|---|---|---|---|---|---|---|---|---|---|---|---|---|
| SN | 90 | 90 | 90 | 90 | 90 | 90 | | 90 | 90 | 90 | 90 | 90 |
| AS | 10 | 9 | 8 | 7 | 6 | 5 | | 9 | 8 | 7 | 6 | 5 |
| CO | | 1 | 2 | 3 | 4 | 5 | | | | | | |
| CA | | | | | | | | 1 | 2 | 3 | 4 | 5 |

| | C49 | C50 | C51 | C52 | C53 | C54 | | C56 | C57 | C58 | C59 | C60 |
|---|---|---|---|---|---|---|---|---|---|---|---|---|
| SN | 90 | 90 | 90 | 90 | 90 | 90 | | 90 | 90 | 90 | 90 | 90 |
| AS | 10 | 9 | 8 | 7 | 6 | 5 | | 9 | 8 | 7 | 6 | 5 |
| CM | | 1 | 2 | 3 | 4 | 5 | | | | | | |
| EP | | | | | | | | 1 | 2 | 3 | 4 | 5 |

| | C61 | C62 | C63 | C64 | C65 | C66 |
|---|---|---|---|---|---|---|
| SN | 90 | 90 | 90 | 90 | 90 | 90 |
| AS | 10 | 9 | 8 | 7 | 6 | 5 |
| GP | | 1 | 2 | 3 | 4 | 5 |

| | C67 | C68 | C69 | C70 | C71 | C72 | | C74 | C75 | C76 | C77 | C78 |
|---|---|---|---|---|---|---|---|---|---|---|---|---|
| SN | 90 | 90 | 90 | 90 | 90 | 90 | | 90 | 90 | 90 | 90 | 90 |
| CO | 10 | 9 | 8 | 7 | 6 | 5 | | 9 | 8 | 7 | 6 | 5 |
| CA | | 1 | 2 | 3 | 4 | 5 | | | | | | |
| CM | | | | | | | | 1 | 2 | 3 | 4 | 5 |

| | C79 | C80 | C81 | C82 | C83 | C84 | | C86 | C87 | C88 | C89 | C90 |
|---|---|---|---|---|---|---|---|---|---|---|---|---|
| SN | 90 | 90 | 90 | 90 | 90 | 90 | | 90 | 90 | 90 | 90 | 90 |
| CM | 10 | 9 | 8 | 7 | 6 | 5 | | 9 | 8 | 7 | 6 | 5 |
| EP | | 1 | 2 | 3 | 4 | 5 | | | | | | |
| GP | | | | | | | | 1 | 2 | 3 | 4 | 5 |

| | C91 | C92 | C93 | C94 | C95 | C96 | | C98 | C99 | C100 | C101 | C102 |
|---|---|---|---|---|---|---|---|---|---|---|---|---|
| SN | 90 | 90 | 90 | 90 | 90 | 90 | | 90 | 90 | 90 | 90 | 90 |
| CA | 10 | 9 | 8 | 7 | 6 | 5 | | 9 | 8 | 7 | 6 | 5 |
| CM | | 1 | 2 | 3 | 4 | 5 | | | | | | |
| EP | | | | | | | | 1 | 2 | 3 | 4 | 5 |

-continued

|    | C103 | C104 | C105 | C106 | C107 | C108 | C110 | C111 | C112 | C113 | C114 |
|----|------|------|------|------|------|------|------|------|------|------|------|
| SN | 90   | 90   | 90   | 90   | 90   | 90   | 90   | 90   | 90   | 90   | 90   |
| EP | 10   | 9    | 8    | 7    | 6    | 5    | 9    | 8    | 7    | 6    | 5    |
| GP |      | 1    | 2    | 3    | 4    | 5    |      |      |      |      |      |
| HP |      |      |      |      |      |      | 1    | 2    | 3    | 4    | 5    |

|    | C115 | C116 | C117 | C118 | C119 | C120 | C122 | C123 | C124 | C125 | C126 |
|----|------|------|------|------|------|------|------|------|------|------|------|
| SN | 90   | 90   | 90   | 90   | 90   | 90   | 90   | 90   | 90   | 90   | 90   |
| EP | 10   | 9    | 8    | 7    | 6    | 5    | 9    | 8    | 7    | 6    | 5    |
| KT |      | 1    | 2    | 3    | 4    | 5    |      |      |      |      |      |
| LP |      |      |      |      |      |      | 1    | 2    | 3    | 4    | 5    |

The above amounts provide exemplary useful amounts ±0.5% for amounts from 1-2%, ±0.5 or 1% for amounts from 3-5%, ±0.5, 1 or 2% for amounts from 6-10%, ±1, 2, 3, 4 or 5% for amounts from 70-90% (with the foregoing percentage ranges being of the total extract amount by weight).

In some embodiments, the solids from the extract(s) typically contribute amounts to the film from one of the following lower endpoints or from one of the following upper endpoints. The lower endpoints are 10, 15, 20, 25 and 30 weight percent. The upper endpoints are 15, 20, 25, 30, 35, 40 and 45 weight percent. The percent of such solids in the adhesive reservoir layer can be, for example, approximately 30.0, 30.1, 30.2 and so in increments of 0.1 up to 40.0.

In some embodiments the herbal bioactive can be one or more flavonoids, isoflavonoids, tocopherols, polyphenols, or similar agents often found in herbal extracts.

Flavonoids can include, for example, flavonols or flavonolols [such as, without limitation, a rutoside: rutin (quercitin 3-O-rutino-side), quercitrin (quercetin 3-O-rhamno-side), isoquercitrin (quercetin 3-O-glucoside), diosmin (diosmetin 7.beta.-rutinoside), astragalin (kaempferol 3-O-glucoside), kaempferol 3-O-rutinoside, myricitrin (or myricetin 3-O-rhamnoside), robinin (or kaempferol 3-O-robinoside 7-rhamnoside), kaempferitrin (or kaempferol 3,7-O-dirhamnoside), nobiletin, tangeretin]. Or, flavonoids can include, for example, flavones [such as, without limitation, rhoifolin (or apigenin 7-O-neohesperido-side), luteolin 7-O-glucoside, scutellarin (or scutellarein 5-O-glucoside), pectolinarin (or pectolinarigenin 7-O-rutoside), galuteolin (or luteolin 5-O-glucoside), acaciin (or acacetin 7-O-rhamnoglu-coside)]. Or, flavonoids can include, for example, flavanones [such as, without limitation, liquiritin (or liquiritin 4'-O-glu-coside), naringin (or naringenin 7-O-neohesperido-side), hesperidin (or hesperetin 7-O-rut-inoside), eriodictin (or eridictiol 7-O-rhamnoside)].

Isoflavonoids can include, for example: formononetin 7-O-glucoside (or ononin), afromosin 7-O-glucoside (or wistin), genistein (or genistein 7-O-glucoside), daidzin, glycitin, genistein 6-O-malonylglucoside, daidzein 6-O-malonylglu-coside, genistein 6-O-acetyl-glucoside, iridin (or irigenin 7-O-glucoside), irisolone, tectoridin (or tectorigenin 7-O-glucoside) or shekanin.

The flavonoids and/or isoflavonoids can be those found in one or more of the herbal extracts identified above, and in amount found in the compositions described above.

If any one of these specific bioactive agents is included in the film it can be used in an amount corresponding to the amount found in one of the above-described extracts.

2. Polymer Components of the Film

The films of the invention are not dissimilar to the films used, for example, to make the Listerine PocketPak mouth fresheners, except that the polymers, polymer amounts, plasticizers and plasticizer amounts are selected to provide a longer residence time. In PocketPak films the polymers used are typically polysaccharide-based or polysaccharide and glycoprotein-based gums such as pullulan, locust bean gum, xanthan gum, sodium alginate, gum Arabic and the like. These can be used in the current films, though generally the overall content of polymer that swell or dissolve more slowly (than in typical mouth freshener films) may be higher.

The films can be comprised in one layer, or two layers. If in two layers, the one adapted to adhere to mucosal tissue when wetted can be termed the "adhesive layer," as can the single layer in a one layer film. With two layers, the outer layer can be less adhesive or non-adhesive, and can provide protection against mechanical agitation, such as agitation by a user's tongue. The components of the outer layer might be, of themselves, less dissolvable than the components of an adhesive layer. However, in the aggregate, the film shall dissolve in that it will transition to fully dissolved parts or parts that will be carried away by normal cleaning processes at the mucosal tissue in question. In forming two layers, diffusion or the forming process itself may provide a gradient in component amounts in the transition between the two layers.

In some embodiments, the polymers contribute amounts to adhesive layers from one of the following lower endpoints (inclusive) or from one of the following upper endpoints (inclusive). The lower endpoints are 20, 25, 30, 35, 40, 45 and 50 weight percent. The upper endpoints are 35, 40, 45, 50, 55, 60, 65, 70, 75 and 80 weight percent. For example, the polymers can comprise 35 to 65 wt. %, or 40 to 60 wt. %. For this purpose polymers comprise synthetic polymers, natural polymer products, or derivatives of natural polymer products, but not polymers that may happen to be found in the plant extracts.

The polymers can be polymers that affect the rate of hydration or mucosal adhesion properties of an adhesive layer. Such polymers can be, for example, carboboxymethylcellulose, cellulose acetate, ethylcellulose, hydroxyethylcellulose, hydroxypropylmethylcellulose (HPMC, such as Pharmacoat 606™, Shin-Etsu Chemical Company Ltd., Japan), nitrocellulose, polyoxyethylene/polyoxypropylene polymers, copolymers or block copolymers, polyvinylpyrrolidone polymers or derivatives, gums such as described above, and the like. Average molecular weight can be selected based on the swelling and dissolution profile sought. Mixtures of less soluble and/or less swellable polymers with more soluble or swellable polymers can help transition the film to a sufficiently dissolved form.

In certain embodiments, the polymer(s) providing mucosal adhesion do not provide adhesion that is as aggressive as adhesion due, for example, to polymer(s) in which Carbopol 940 is the major adhesive polymer (such as comprising 40% by wt. or more of an adhesive composition). In certain embodiments, the film is not immediately adhesive, but becomes adhesive as it acquires moisture from mucosal tissue, with the polymer(s) and other components of the film selected to provide such less aggressive adhesion.

In certain embodiments, the film comprises carbamer, polyethylene oxide, ethylcellulose, titanium oxide and colorant (such as F, D and C blue lake colorant). Often the film is formed using a pharmaceutically appropriate solvent such as ethanol, water, mixtures, or the like. Such solvents are typically largely evaporated away prior to use.

3. Plasticizers, Other Components

Plasticizers, penetration enhancers, flavoring agents, preservatives, coloring agents, and the like can be included in the film. Plasticizers will generally modify the feel, softness, flexibility (in an un-wetted state) of the film. Penetration enhancers may, in some cases, act as plasticizers. Examples of plasticizers include, without limitation, glycerol, propylene glycol, fatty acid esters (such as glyceryl oleate), and the like. Examples of penetration enhancers include, without limitation, PEG-[C10-C30]alkyl, N-lauroyl sacrcosine, sorbitan monolaurate, stearyl methacrylate, N-Dodecylazacycloheptan-2-one, N-dodecyl-2-pyrrolidinone, N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 2-dodecyl-2-oxo-1-pyrrolidineacetic acid, 1-azacylioheptan-2-one-dodecylacetic acid, and the like.

4. Illustrative Indications; Treatment Parameters

Indications treated with the methods and devices of the invention include any indication of mucosal tissue, or tissue sufficiently adjacent to mucosal tissue, treatable with the plant extracts and/or described antimicrobial agents. For example, oral indications and microbial indications (such as microbial lesions) can be treated with the methods and devices.

Oral indications appropriate for treatment with the invention include, without limitation, periodontal disease, gingivitis, aphthous ulceration (e.g., canker sores, recurrent apthhous stomatitis, recurrent ulcerative stomatitis), mechanical trauma, thermal trauma, the oral lesions, dry mouth (xerostomia), mucositis or eruptions of lichen planus, bullous pemphigoid, pemphigus vulgaris, dermatitis herpetiformis or angular chelitis, recurrent herpes, other microbial (including viral) eruptions of the oral mucosa, lesions (including the foregoing and such as mucositis) secondary to chemotherapy or radiation treatment, lesions resulting from trauma (including chemical or other burns), lesions secondary to systemic disease, lesions resulting from autoimmune disease, lesions with idiopathic causes, or the like. The herbal component of the film typically includes components selected to reduce inflammation. In certain embodiments, the herbal component is effective to reduce matrix metalloprotease(s) expressed at or near the mucosal membrane, and/or to reduce cytokine(s) expressed at or near the mucosal membrane.

The film will generally be applied multiple times during the day, as indicated by the residence time of the film, the period of sustained release of bioactive agent(s), and the like.

In the case of mucositis secondary to chemotherapy or radiation treatment, the film can be administered after the primary treatment, but before symptoms of mucositis are apparent.

In many embodiments, the treated tissue is in the mouth. In other embodiments, the treatment tissue is at or adjacent to other mucosal tissue, such as nasal, anal, vaginal, and the like.

To provide physical protection for the diseased tissue, and to provide time for delivering medicament, the films in some embodiments have a mucosal residence time (defined below) of 5 minutes or more, 10 minutes or more, 15 minutes or more, 30 minutes or more, 60 minutes or more, 1.5 hours or more, 2 hours or more, or 3 hours or more.

5. Applicator

A film applicator kit 10 is exemplified in FIG. 1. Film 11 is attached to applicator 16 via junction 15. The junction 15 can be of any number of forms that allow the film to be carried by the applicator, but which can be torn, peeled, broken after the film begins to adhere to mucosal tissue. For example, it can be a heat-initiated weld, it can be a lamination (by heat, adhesive, or the like) to a part of a film that is part of or contiguous with the film to be applied, or the like. The junction can be weakened, by perforation or thinning to facilitate separating the film and the applicator after the film has been or begun to be applied.

Other applicator examples are shown in FIGS. 2A, 2B (kit 20, film 21, applicator 26), 3A, 3B (kit 30, film 31, applicator 36). It will be apparent that applicator can come in many shapes and sizes adapted to help a user manipulate the film to place it against a mucosal surface.

FIG. 4A shows a film applicator kit 60 with an applicator 66 having handle 67, which handle can be an open ring sized to fit the top of index finger to aid a user in positioning the film 61. FIG. 4B shows a film applicator kit 70 with an applicator 76 having handle 77, which handle can be an open ring sized to fit the top of an index or other finger to aid a dental worker in positioning the film 71. Additionally, handle 76 incorporates a swivel member 76A that allows the film to rotate with respect to the handle 77. As will recognized, the swivel member can be located anywhere on applicator 76. Swivel member 76A can be, for example, a sleeve in which an axle (e.g., the rest of applicator 76) rotates, or an axle about which a sleeve connected to the rest of applicator 76 rotates. Any device for facilitating rotation can be used, including devices with bearings or other friction-reducing mechanisms. Permitted rotation can be 360 degrees, or a narrower range adapted to facilitate localizing the film on mucosal tissue.

The applicator allows the film to be positioned relatively precisely—as can be especially useful to match the location of affected tissue with the film, which can be relatively small (e.g., 1 cm diameter). The applicator kit(s) can be individually packaged, for example in foil or polymer packets. These can, for example, be opened by tearing, such as from a scored starting location.

The applicator can be used with a wide variety of films intended to be adhered to mucosal tissue. As such, the films can delivery any of a variety of bioactive agents, such as antimicrobial agents. Or, the films can delivery a cosmetic agent, such as a freshener.

6. Film Subsections

In certain embodiments, the film has weakened segments 42, 52 (FIGS. 5A, 5B) that allow, for example, film 41, 51 to be torn into subsections (such as subsections 41A-F, 51A-F). The segments can, for example, be weakened by thinning, perforation, or the like. The subsections can be used to help appropriately size a film for use. With partial scores, such as weakened segments 52, a user can have more flexibility in selecting the final shape.

7. Other Solid Dosage Forms or Rinse for Use with the Film

In certain embodiments, the film is administered in conjunction with another administration form, such as a patch or mucoadhesive solid dosage form. This other dosage form can be applied before, concurrently, or after administration of the film. Other solid forms can help deliver medicament to more severely affected, or more mechanically accessible tissue, while the film delivers medicament elsewhere.

8. Antiinflamatory Agents

In certain embodiments, the film further comprising anti-inflammatory agent(s), such as steroidal or nonsteroidal anti-inflammatory agents. Steroidal anti-inflammatory agents, include but are not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Other anti-inflammatory agents useful in the compositions include the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference can be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974).

Specific non-steroidal anti-inflammatory agents useful in the composition invention include, but are not limited to: 1) the oxicams, such as piroxicam, isoxicam, tenoxicam, sudoxicam, and CP-14, 304; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; 6) the pyrazoles, such as phenylbutazone, oxyphenbutazone, feprazone, azapropazone, and trimethazone; and mixtures of the foregoing.

Mixtures of these steroid and/or non-steroidal anti-inflammatory agents can be employed, as well as the pharmacologically acceptable salts and esters of these agents. For example, etofenamate, a flufenamic acid derivative, is particularly useful for topical application.

The following examples further illustrate the present invention, but of course, should not be construed as in any way limiting its scope.

DEFINITIONS

The following terms shall have, for the purposes of this application, the respective meanings set forth below.

Antimicrobial Agent

An antimicrobial agent is a bioactive agent that inhibits the reproduction or decreases the survival of pathogenic microbes (e.g., a bacteria, mycoplasma, fungi including but not limited to yeast, virus, protozoa or parasite (such as a nematode, schistosome, malaria parasite)) or inhibits the propagation, which includes without limitation replication, viral assembly or cellular infection, of a virus.

Bioactive Agent

A bioactive agent is a substance such as a chemical that can act on a cell, virus, tissue, organ or organism, including but not limited to insecticides or drugs (i.e., pharmaceuticals) to create a change in the functioning of the cell, virus, organ or organism.

Dissolvable Polymers

Dissolvable polymers are polymers which, in the aggregate, dissolve completely or sufficiently so that any residual polymer is readily suspended in mucosal fluids.

Effective Amount

To treat the indications of the invention, an effective amount of a pharmaceutical compound will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Thus, an effective amount can be, for example, an amount that reduces the severity or duration of oral lesions, ulcerations, bleeding, irritation, swelling, erythema, or the like.

Mucosal Residence Time

The mucosal residence time is the time it takes a film to dissolve (taking into account the meaning for "dissolve" implied by the definition of "dissolvable polymers) when placed on an appropriate mucosal surface (which may depend on the target site for the film's use), assuming no directed mechanical action, such as with a user's tongue.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of treating an indication of mucosa tissue comprising administering to the affected mucosal tissue a dissolvable film comprising: a) an antiinflammatory amount of an extract of *Sambucus nigra* and one or more of a
    second extract of *Calendula officinalis, Allium sativum, Camellia sinensis, Centella asiatica, Commiphora molmol, Echinacea purpurea, Gaultheria procumbens, Hypericum perforatum, Krameria triandra, Ligusticum porterii-osha, Matricaria recutita, Melissa officinalis, Salix alba, Thymus vulgaris, Uncaria tomentosa, Usnea barbata* or *Vaccinium myrtillus;*
    b) an adhesive layer comprising:
    50% or more by weight polymer(s) comprising an adhesion-promoting amount of carbamer and one or more soluble polymers,
    wherein the adhesive layer becomes adhesive as it is placed against a mucosal surface and begins to absorb moisture therefrom, and the adhesion of the adhesive layer is less aggressive than would pertain for an adhesive layer consisting of polymers including 40% or more by weight of Carbopol 940 and said antiinflammatory amount of said extracts,
    and wherein the extracts are substantially comprised in the adhesive layer; and
    c) a less adhesive protective layer, wherein the protective layer has polymers selected
    to be, on the whole, relatively less dissolvable than those of adhesive layer;
    wherein the film, when placed on a mucosal surface, dissolves away completely after 15 minutes or more and dissolution is such that such film can be applied to a mucosal lesion two or more times per day without film removal from the lesion,
    wherein the film has only the two layers, and wherein the film, if periodically applied to
    the mucosal indication, is effective in ameliorating said indication.

2. The method of claim 1, wherein the indication is of the oral cavity.

3. The method of claim 2, wherein the indication is periodontal disease, mechanical trauma, thermal trauma, xerostomia, mucositis, eruptions of lichen planus, bullous pemphigoid, pemphigus vulgaris, dermatitis herpetiformis or angular chelitis, microbial eruptions of the oral mucosa, lesions resulting from trauma, lesions secondary to systemic disease, or lesions resulting from autoimmune disease.

4. The method of claim 2, wherein the indication is periodontal disease.

5. The method of claim 2, wherein the indication is gingivitis.

6. The method of claim 2, wherein the indication is eruptions of lichen planus, bullous pemphigoid, pemphigus vulgaris, dermatitis herpetiformis or angular chelitis.

7. The method of claim 2, wherein the indication is a lesion resulting from trauma.

8. The method of treating an indication of the mucosa of claim 1, wherein the mucosa is anal or vaginal mucosa, and wherein the film, if periodically applied to the indication of anal or vaginal mucosa, is effective in ameliorating said indication.

9. The method of claim 8, wherein in the film dissolves away completely after 30 minutes or more.

10. The method of claim 8, wherein in the film said extracts of *Sambucus nigra* comprises 51 to 100% by weight of the extracts in the film.

11. The method of claim 10, wherein in the film the second extract comprises from 1 to 50% by weight of extracts in the film.

12. The method of claim 11, wherein in the film there is a third extract that comprises from 0.5 to 5% by weight of extracts in the film.

13. The method of claim 12, wherein the third extract is of *Centella asiatica*.

14. The method of claim 10, wherein in the film the second extract is of *Calendula officinalis* and comprises from 1 to 50% by weight of extracts in the film.

15. The method of claim 14, wherein in the film there is a third extract that comprises from 0.5 to 5% by weight of extracts in the film.

16. The method of claim 15, wherein the third extract is of *Centella asiatica*.

17. The method of claim 8, the film further comprising one or more non-herbal anti-inflammatory agents.

18. The method of claim 8, wherein the film comprises an antiinflammatory effective amount of component(s) of *Sambucus nigra* and *Calendula officinalis*.

19. The method of claim 8, wherein the film comprises an antiinflammatory
    effective amount of component(s) of *Sambucus nigra, Calendula officinalis* and *Centella asiatica*.

* * * * *